Figure 1:
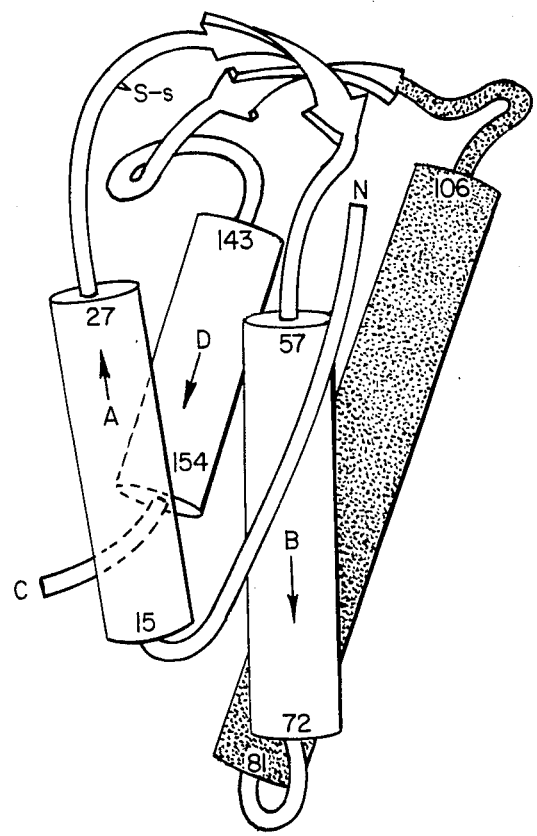
Figure 1:
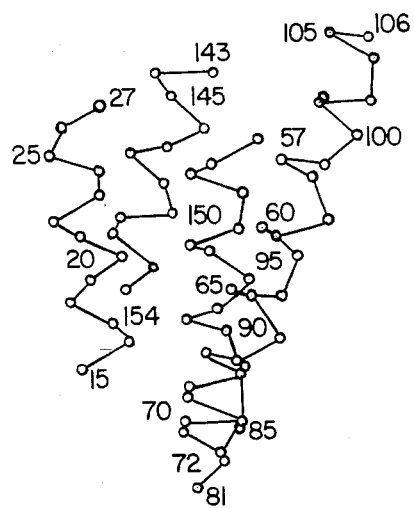
Figure 1:
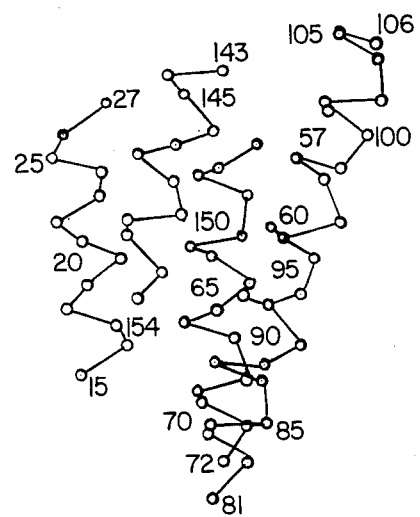

United States Patent [19]

Bell et al.

[11] Patent Number: 4,753,795

[45] Date of Patent: Jun. 28, 1988

[54] MODIFIED (80-113) BETA INTERFERONS

[75] Inventors: Leslie D. Bell, Thame; John C. Smith; Paul G. Boseley, both of High Wycombe, all of United Kingdom; Michael Houghton, Danville, Calif.

[73] Assignee: G. D. Searle & Co., Chicago, Ill.

[21] Appl. No.: 623,601

[22] Filed: Jun. 22, 1984

[30] Foreign Application Priority Data

Jul. 1, 1983 [GB] United Kingdom ............... 8317880

[51] Int. Cl.⁴ .................. A61K 45/02; C07K 15/26; C07K 13/00; C12P 21/00
[52] U.S. Cl. ...................................... 424/85; 530/351; 435/68; 435/811; 435/172.3
[58] Field of Search .................... 424/85; 530/351; 435/68, 172.3

[56] References Cited

U.S. PATENT DOCUMENTS

| | | | |
|---|---|---|---|
| 4,414,150 | 8/1983 | Goeddel | 435/70 |
| 4,569,908 | 2/1986 | Mark et al. | 435/71 |
| 4,588,585 | 5/1986 | Mark et al. | 435/172.3 |

OTHER PUBLICATIONS

Shepard et al., Nature, vol. 294, pp. 563-565, 1981.

Primary Examiner—Blondel Hazel
Attorney, Agent, or Firm—Mary Jo Kanady; Paul D. Matukaitis

[57] ABSTRACT

Modified beta interferons containing amino acid substitutions in the beta interferon amino acids 80 to 113 are described. These modified beta interferons exhibit changes in the antiviral, cell growth regulatory or immunomodulatory activities when compared with unmodified beta interferon.

9 Claims, 1

MODIFIED (80-113) BETA INTERFERONS

BACKGROUND OF THE INVENTION

1. Field of the Invention

This invention describes the use of recombinant DNA technology for the design and synthesis of novel, modified interferons. More specifically the invention relates to interferons not known in nature which are intended for use in viral and neoplastic diseases, and immunosuppressed and immunodeficient conditions.

2. Description of the Prior Art

The interferons are a class of proteins that occur in vertebrates and act as biological regulators of cell function which include increasing resistance to pathogens, limiting cell growth and modulating the immune system. The most studied property of the interferons is their ability to convert cells into an "antiviral state" during which they are more resistant to virus replication (Lengyel, Annual Review of Biochemistry, 51, 251, 1982). In addition to conferring antiviral resistance to target cells, interferon (IFNs) have antiproliferative (antigrowth) properties (Stewart, 1979, The Interferon System, Springer Berlin) It has cleary been shown that interferons produced naturally act as antiviral and antiproliferative agents (Gresser et al, Biochim. Biophys. Acts, 516, 231, 1978; J. Exp Med, 144, 1316, 1976).

The IFNs by virtue of their antigenic biological and physico-chemical properties, may be divided into three classes: type I, IFN-$\alpha$ ("Leucocyte") and IFN-$\beta$ ("fibroblast"); and type II IFN-$\gamma$ ("immune") (Stewart et al, Nature, 286, 10, 1980). Both genomic DNA and cDNA clones of type I and type II IFNs have been isolated and sequenced, and the potential protein sequences deduced (e.q. Pestka, Arch. Biochem. Biophys., 221, 1, 1983). Whilst in man only one IFN-$\beta$ and IFN-$\gamma$ gene are known, human IFN-$\alpha$ is specified by a multigene family comprising at least 20 genes. The classification of IFN-$\beta$ and IFN-$\alpha$ as type I interferons is in part determined by their significant degree of homology, >23% at the protein level (Taniquchi et al, Nature, 285, 547. 1980).

Whilst the mechanism of action of interferons is not completely understood, certain physiological or enzymatic activities respond to the presence of the interferons. These activities include RNA and protein synthesis. Among the enzymes induced by interferons is (2'-5') (A)n synthetase which generates 2'-5' linked oligonucleotides, and these in turn activate a latent endoribonuclease, RNAse L, which cleaves single-strand RNA, such as messenger RNA (mRNA) and ribosomal RNA (rRNA). Also induced by IFNs is a protein kinase that phosphorylates at least one peptide chain initiation factor and this inhibits protein synthesis (Lengyel, ibid. p. 253) IFNs have been shown to be negative growth regulators for cells by regulation of the (2'-5') An synthetase activity (Creasey et al, Mol. and Cell Biol, 3, 780, 1983). IFN-$\beta$ was indirectly shown to be involved in the normal regulation of the cell cycle in the absence of inducers through the use of anti-IFN-$\beta$-antibodies. Similarly, IFNs have been shown to have a role in differentiation (Dolei et al, J. Gen. Virol., 46, 227, 1980) and in immunomodulation (Gresser, Cell. Immunol., 34, 406, 1977). Finally, IFNs may alter the methylation pattern of mRNAs and alter the proportion of fatty acids in membrane phospholipids, thereby changing the ridigity of cell membranes.

These and other mechanisms may respond to interferon-like molecules in varying degrees depending on the structure of the interferon-like polypeptide. Preliminary evidence (U.K. Pat. No. GB 2 090 258A) suggests that members of the multigene IFN-$\alpha$ family vary in the extend and specificity of their antiviral activity (Pestka ibid.). For example, combination of IFN-$\alpha$A with IFN-$\alpha$D resulted in "hybrid" genes which show antiviral properties that are distinct from either parent molecule (Weck et al, Nucl. Acids Res., 9, 6153, 1981; De La Maza et al, J. IFN Res., 3, 359, 1983; Fish et al, Biochem. Biophys. Res. Commun., 112, 537, 1983; Weck et al, Infect Immun., 35, 660, 1982). However, hybrid human IFNs with significantly increased human cell activity/specificity have not yet been developed. One patent has been published describing IFN-$\beta$/$\alpha$ hydrids (PCT/U.S. No. 83/00077). This patent described three examples, none of which have significantly improved activity. The three examples were constructed using two naturally occurring restriction sites. The resulting hybrid inteferons were (1) alpha 1 (1–73)-beta (74–166); (2) beta (1–73)-alpha 1 (74–166); and (3) alpha 61A (1–41)-beta (43–166). These three examples differ structurally from the examples of the present invention. These three examples were based upon the accidental location of two restriction sites and not upon the intentionally designed DNA and amino acid sequences of the present invention.

It is envisaged that a modified interferon will display a new advantageous phenotype. The design and synthesis of new interferon-like polypeptides composed of portions of IFN-$\beta$ and other amino acid sequences is advantageous for the following reasons:

1. New IFNs can be created which show a greater antiproliferative to antiviral activity (and vice versa) resulting from the selective activation of only some of the normal interferon-induced biochemical pathways.
2. The affinity of hybrid or modified IFNs for cell surface receptors can differ from that of naturally occurring interferons. This will allow selective or differential targeting of interferons to a particular cell type, of increased affinity for the receptor—leading to increased potency against a particular virus disease or malignancy.
3. It will be possible to design novel IFNs which have an increased therapeutic index, thus excluding some of the undesirable side effects of natural IFNs which limit their use (Powledge, T.M., Biotechnology, 2, 214, March 1984).
4. Novel IFNs can include in the design structures which allow increased stability to proteolytic breakdown during microbial synthesis.
5. Novel IFNs can be designed to increase their solubility or stability in vivo, and prevent non-specific hydrophobic interactions with cells and tissues.
6. Novel IFNs can be designed which are more readily recovered from the microbial supernatant or extract and more easily purified.

Additional Relevant Patent Applications

U.K. No. GB 2 116 566A—Animal interferons and processes for their production.
U.S. No. 4,414,150—Hybrid human leukocyte interferons
U.K. No. GB 2 068 970A—Recombinant DNA technique for the Preparation of a protein resembing human interferon.

SUMMARY OF THE INVENTION

Recombinant DNA technologies were successfully applied to produce modified beta interferon-like polypeptides, nucleic acids (either DNA or RNA) which code for these modified beta interferons, plasmids containing the DNA coding for the modified beta interferons and procedures for the synthesis of these modified beta interferons. Each of the amino acids 80-113 of human beta interferon may individually be replaced by any other amino acid. This replacement may be accomplished in groups of four to thirty-three amino acids. One preferred embodiment is the replacement of four to twenty-four of the amino acids 82 to 105 of human beta interferon by four to twenty-four other amino acids Another preferred embodiment is the replacement of beta interferon amino acids 103–112 by four to ten other amino acids.

The beta interferon amino acids 103–112 may be replaced sequentially by corresponding human alpha interferon amino acids. Correspondence is defined by usage in this invention. Among the alpha interferons are alpha 1, alpha 2 and alpha H. The alpha and beta interferons from any mammal may be used including but not limited to humans or other primates, horses, cattle, sheep, rabbits, rats, and mice. In one embodiment of the invention, the leucine occurring at position 84 in human beta interferon may optionally be replaced by proline. Yet another embodiment of the invention discloses the use of the modified beta interferons where in one or more of the antiviral, cell growth regulatory, or immunomodulatory activities is substantially changed from that of the unmodified beta interferon. Particularly preferred embodiments are the amino acid sequences of IFNX405, 423, and 429. Yet another preferred embodiment of the invention is DNA or RNA sequences which code for the synthesis of IFNX405, 424, or 429. Still another embodiment is a plasmid or a cell containing a DNA sequence capable of coding for the synthesis of IFNX405, 423, or 429. Yet another embodiment of the invention is a pharmaceutical composition continuing an efective amount of IFNX405, 423, or 429. A final embodiment of the invention is the use of pharamaceutical compositions containing the modified beta interferons in a method of treating viral infections, regulating cell growth or regulating the immume system.

The modified interferons have altered activities measurable in vitro such as antiviral or immunomodulatory activity. Target cell specificity can also be altered.

An increased target cell specificity can result in an improved therapeutic index. This should exclude some of the side effects caused by the use in humans of naturally occurring IFNs.

This invention relates to the production in sufficient amounts of novel, highly specific interferon-like molecules suitable for the prophylactic or therapeutic treatment of humans—notably for viral infections, malignancies, and immunosuppressed or immunodeficient conditions.

BRIEF DESCRIPTION OF THE CHARTS AND TABLES

FIG. 1 shows the Sternberg-Cohen 3D model of $\alpha_1$ and $\beta$ interferons (Int. J. Biol. Macromol, 4, 137, 1982).

Chart 2 (a to c) shows the ligated oligonucleotides used in the construction of the novel, modified IFNs.

Chart 3 (a to d) shows the complete necleotide sequences of the novel, modified IFn genes and the encoded amino acid sequences.

Chart 4 shows the nucleotide sequence of the trp promoter used to initiate transcription of the novel, modified IFN genes.

Table 1 compares expression, antiviral and antiproliferative activity for IFNX423, IFNX429, and IFN-$\beta$ present in crude bacterial extracts.

DESCRIPTION OF THE PREFERRED EMBODIMENTS

Introduction

The IFN-$\beta$ gene is a unique gene but shows some significant homologies to the multigenic IFN-$\alpha$ family (Rubinstein, Biochim. Biophys. Acta, 695, 5, 1982). Sternberg and Cohen (Int. J. Biol. Macromol., 4, 137, 1982) have proposed a similar secondary structure for IFN-$\beta$ and IFN-$\alpha_1$. Structure prediction studies suggest four $\alpha$-helices which can be "packed" into a right handed bundle (FIG. 1) similar to that observed in several unrelated protein structures as determined by X-ray crystallography. The design of some of the modified interferons described herein is derived from our interpretation of the Sternberg/Cohen mode. Since IFNs $\beta$ and $\alpha$ are believed to bind to the same receptor at the cell surface it is possible to introduce variability into IFN-$\beta$ by replacing specific areas with IFN-$\alpha$ segments.

The field of the present invention is the design, synthesis and characterization of interferon-like molecules related to IFN-$\beta$ which may have sequences between amino acids residues 85–115 replaced with any other amino acid sequence, unrelated protein sequences, or sequences similar to those of IFN-$\alpha$'s, IFN-$\beta$'s or IFN-$\gamma$ found in mammals and other vertebrates.

Each amino acid in the 80 to 113 region can be replaced by any other naturally occurring amino acids. The naturally occurring amino acids and their nomenclature are: alanine (Ala or A); valine (Val or V); leucine (Leu or L); isoleucine (Ile or I); proline (Pro or P); phenylalanine (Phe or F); tryptophan (Trp or W); methionine (Met or M); glycine (Gly or G); serine (Ser or S); threonine (Thr or T); cysteine (Cys or C); tyrosine (Tyr or Y); asparagine (Asn or N); glutamine (Glu or Q); aspartic acid (Asp or D); glutamic acid (Glu or E); lysine (Lys or K); arginine (Arg or R); and histidine (His or H).

Though binding of hybrid IFN-$\beta$'s ($\alpha_1$ and $\alpha_2$ in Streuli et al, Proc. Natl. Acad. Sci. USA, 78, 2848, 1981), an attempt was made to analyse the number and nature of idiotypes involved in the receptor binding site of IFN-$\alpha$'s. Two sites were proposed as constituting the binding site, one in the amino-terminal half and the other in the carboxy-terminal half of IFN-$\alpha$. The two major regions of partial homology between IFN-$\alpha$'s the IFN-$\beta$ occur between amino acid residues 28–80 and 115–151 which may well correspond to the above mentioned idiotypes. Evidence that the 28–80 region may be important in receptor binding come from the finding that polyclonal antibodies raised against a synthetic peptide composed of IFN-$\alpha_2$ amino acids 24–81, bind to IFN-$\alpha_2$ and prevent it interacting with its cell receptor (Dreiding, TNO Interferon Meeting, Rotterdam, 1983).

Little or no information is available on the function or importance of the region of IFN-$\beta$ or IFN-$\alpha$'s between amino acid residues 82 and 115 (IFN-$\beta$ numbering), which includes a computer-predicted α-helical region (Sternberg and Cohen, Int. J. Biol. Macromol., 4, 137, 1982).

However, an amino terminal fragments of IFN-$\alpha_2$ of 110 amino acids (Ackerman et al, Proc. Natl. Acad. Sci. USA, 81, 1045, 1984) retains a small portion of its antiviral activity. C-terminal fragments are not active.

The following are examples of novel, modified IFNs with amino acid replacements in the 82–115 region of IFN-β to illustrate the invention, and are not intended to limit the scope of the invention in any way. Below are described techniques used in the design, chemical synthesis and insertion of DNA fragments in the 82–115 region of the human IFN-β gene. The resultant novel, modified IFNs are hereafter described as group III IFNs. Decreased antiviral and/or immunostimulating activity are among the altered properties shown by some of the group III novel IFNs with amino acid replacements in the 82–115 region. The techniques described will be familiar to anyone skilled in the art [see also Molecular Cloning, A Laboratory Manual, eds. Maniatis et al, Cold Spring Harbor Laboratories].

Design of the synthetic gene fragments

The nucleotide sequences of each synthetic DNA fragment (Charts 2a to c) were designed utilizing the following criteria:

1. Codon utilization (where it deviates from natural IFN-β gene sequence) was optimized for expression in *E.coli.* Natural IFN-β gene sequences were used as far as possible in order to obtain levels of expression of novel IFNs as high as that of IFN-β from plasmid pGC10 (see Table 1). pGC10 (~4,440 bp) expresses the natural IFN-β gene at a high level and is identical to p1/24 (Patent Application GB 2 068 970A, hereby incorporated by reference) except for the ribosome binding site sequence shown in Chart 4 and the deletion of the ~546 bp BglII-BamHI fragment.
2. Sequences which might anneal to each other in the assembly of the chemically synthesized fragment (Chart 2) were not included in the design (within the limits allowed by the redundancy in the genetic code).

Chemical Synthesis of Gene Fragments

Oligodeoxyribonucleotides were synthesized by the phosphoramidite method (M. H. Caruthers in "Chemical and Enzymatic Synthesis of Gene Fragments", ed. H. G. Gasen and A. Lang, Verlag Chemie, 1982, p. 71) on controlled pore glass (H>Koster et al, Tetrahedron, 40, 103, 10984). Fully protected 2'-deoxyribonucleotide 3'-phosphoramidites were synthesized from the protected deoxyribonucleotide and chloro-N,N-(diisopropylamino)methoxyphosphine (L. J. McBride and M. H. Caruthers, Tetrahedron Lett., 24, 245, 1983 and S. A. Adams et al, J. Amer. Chem. Soc., 105, 661, 1983). Controlled pore glass supports were synthesized as described (F. Chow et al, Nuc. Acids Res., 1981, 9, 2807) giving 30–50 μmol deoxynucleoside per gram.

The functionalised controlled pore glass (50 mg) was treated in a sintered glass funnel at ambient temperature sequentially with:

1. Dichloromethane (3 ml, 10s)
2. 3% (v/v) dichloroacetic acid in dichloromethane (2 ml, 120s)
3. dichloromethane (3 ml, 10s)
4. anhydrous acetonitrile (3 ml, 10s)
5. phosphoramidite monomer (0.06M)/tetrazole (0.23M) in anhydrous acetonitrile (1 ml, 120s)
6. acetonitrile (3 ml, 10s)
7. dimethylaminopyridine (0.07M) in acetic anhydride/2,6-lutidine/acetonitrile (1/2.6 v/v) (1 ml, 60s)
8. acetonitrile (3 ml, 10s)
9. iodine (0.2M) in 2,6-lutidine/tetrahydrofuran/water (1/2/2 v/v) (1 ml, 30s)
10 acetonitrile (3 ml, 10s)

The cycle was repeated with the appropriate phosphoramidite monomer until the immunogenetic chain was complete. The coupling efficiency of each cycle was monitored by spectrophotometric assay of the liberated dimethoxytrityl alcohol in 10% (w/v) trichloroacetic acid/dichloromethane at 504 nm. After completion of the synthesis, the protecting groups were removed and the oligomer cleaved from the support by sequential treatment with 3% (v/v) dichloroacetic acid/dichloromethane 9120s, thiophenol/triethylamine/dioxan (1/1/2 v/v) (1h) and concentrated ammonia at 70° C. (4h). The deprotected oligonucleotides were purified either by HPLC on a Partisil 10 SAX column using a gradient from 1M to 4M triethylammonium acetate pH 4.9 at 50° C. or by electrophoresis on a denaturing 15% polyacrylamide gel (pH 8.3).

Ligation of Oligonucleotide Blocks 500 pmole aliquots of the oligonucleotides were phosphorylated with 1 unit of T4 induced polynucleotide kinase in 20 μl of a solution containing 1000 Ci/pmole [$^{32}$p]γ-ATP (2.5 Ci/mMole), 100 μM sperimidine, 20 mM DTT, 10 mM $MgCl_2$, 50 mM Tris-HCl (pH 9.0) and 0.1 mM EDTA for 60 minutes at 37° C. The mixtures were then lyophilized and each oligonucleotide purified in a denaturing 15% polyacrylamide gel (pH 8.3). After elution from the gel, the recovery was determined by counting the radioactivity.

Blocks (length 30–50 bases) were assembled by combining 25 pmole of each phosphorylated component with equimolar amounts of the unphosphorylated oligomers from the complementary strand. The mixtures were lyophilized and then taken up in 15 μl water and 2 μl 10× ligase buffer (500 mM Tris-HCl pH 7.6, 100 mM $MgCl_2$). The blocks were annealed at 100° C. for 2 minutes, then slowly cooled to room temperature (20° C.). 2 μl 200 mM DTT and 0.5 μl 10 mM ATP were added to give final concentrations of 20 mM DTT and 250 μM ATP in 20 μl. 1.25 units of T4 DNA ligase were also added. After 18 hours at 20° C., the products were purified in a 15% polyacrylamide gel under denaturing conditions.

Two duplex blocks were then constructed from the single-stranded pieces. (These were 150 base pairs and 75 base pairs). 1.5 pmole of each block were taken and the mixtures lyophilized. Annealing was carried out in 15 μl water and 2 μl 10× ligase buffer at 100° C. for 2 minutes, then slowly cooled to 10° C. 2 μl 200 mM DTT, 0.5 μl 10 mM ATP and 1.25 units T4 DNA ligase were added. The reaction was left at 10° C. for 18 hours. The products were then purified in a 10% native polyacrylamide gel.

The final product was assembled by combining 0.4 pmole of the two duplexes. The mixture was lyophilized and then taken up in 15 μl water and 2 μl 10× ligase buffer. It was annealed at 50° C. for 2 minutes and then slowly cooled to 10° C. 2 μl 20 mM DTT, 0.5 μl 10 mM ATP and 1.25 units ligase were then added and the reaction left at 10° C. for 18 hours. The final product was purified in a 5% native polyacrylamide gel. After elution and ethanol precipitation, the product was taken up in 10 μl water. 0.5 μl were removed for counting to calculate the recovery. 2 μl 10×ligase buffer, 2 μl 200 mM DTT, 2 μl 1 mM spermidine, 1 μl 10 mM ATP, 3 μl water and 0.5 units kinase were added to the rest (total volume 20 μl). The reaction was left at 37° C. for 1 hour and stopped by heating at 90° C. for 2 minutes. The final product was ethanol precipitated.

Construction of plasmids expressing novel, modified interferons

This section lists and identifies the vectors employed in the cloning of the synthetic DNA fragments (Chart 2) into the IFN-β coding region, the restriction enzyme sites* used for the insertion, and the rationale for the construction. The positions of these sites* are shown relative to the complete coding nucleotide sequences of the group III novel IFN genes (Chart 3). The IFN-β (or novel IFN) coding region is shown as a heavy line and would be translated from left to right. The vector sequences between the BamHI site and the EcoRI site are the same as those in pAT153 (equivalent to pBR322 with a 705bp HaeII fragment deleted-nucleotides

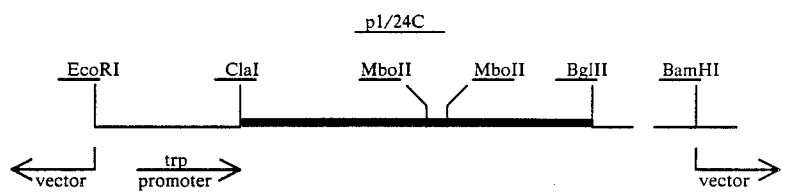

1,646–2,351 on the map). The E. coli trp promoter (Chart 4) lies between the EcoRI site and ClaI site.

1. IFNX423 IFN-$\beta[\beta^{82-105} \rightarrow \alpha_1^{80-103}][\text{Leu}^{84} \rightarrow \text{Pro}]$ This novel, modified IFN was designed to determine the effect(s) of replacing the computer-predicted C β-helix of IFN-β with that of IFN-$\alpha_1$ on antiviral, antiproliferative and immunostimulating activities (Sternberg and Cohen, Int. J. Biol. Macromol., 4, 137, 1982). Also, what would be the effect of shortening this α-helix by introducing a proline at residue 84?

Starting vector: pGC206. This vector expresses IFN-β from a part natural (amino acids 1–46) and part synthetic IFN-β gene (amino acids 47–166 and (Chart 3c). It was constructed by replacing the 257bp E.coRI-PvuII fragment of pMN47 with the equivalent fragment from pl/24C. pMN47 contains an entirely synthetic IFN-β gene (Chart 3c) inserted between the ClaI and BamHI sites of pl/24C, the plasmid containing the entirely natural IFN-β gene. (pl/24C is identical to pl/24 (UK Patent Application No. GB 2 068 970A) except for the underlined sequences in Chart 4).

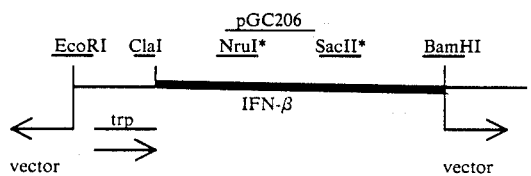

A synthetic oligonucleotide (Chart 2a) was inserted between the NruI* and SacII* sites of pGC206 to give the nucleotide sequence shown in Chart 3a. The resultant IFNX423 gene is expressed from plasmid pGC215.

2. IFNX429 IFN-$\beta[\beta^{82-105} \rightarrow \alpha_1^{80-103}]$

The rationale and starting vector was the same as for IFNX423 above. In IFNX429 the predicted α-helical region (82–105) was not shortened by the introduction of proline at amino acid residue 84. A synthetic oligonucleotide (Chart 2b) was inserted between the NruI* and SacII* sites of pGC206 to give the nucleotide sequence shown in Chart 3b. The resultant IFNX429 gene is expressed from plasmid pGC2154.

3. IFNX405 IFN-$\beta[^{103-112} \rightarrow \alpha_1^{101-110}]$

This novel, modified IFN was designed to determine the effect(s) of replacing a relatively non-conserved region (IFN-β cf. IFN-$\alpha_1$) on antiviral, antiproliferative and immunostimulating activities.

Starting vector: pl/24C This vector expresses mature IFN-β and is identical to pl/24 except for the ribosome binding site sequence underlined in Chart 4.

A synthetic oligonucleotide (Chart 2c) was inserted between the MboII* sites (cut sites equivalent to amino acids 102 and 113) of pl/24C to give the nucleotide sequence shown in Chart 3d. The resultant IFNX405 is expressed from plasmid pXX405.

Expression of novel, modified IFNs in Escherichia coli

All the above mentioned plasmids were grown i E. coli HB101 in the presence of a low level of tryptophan to an OD$_{600}$ of 0.5, then induced for IFN synthesis. The medium (200 ml) contained: M9 salts, 0.5% glucose, 0.1 mM CaCl$_2$, 0.5% Casamino acids, 1 mM MgSO$_4$, 0.1 mg/ml vitamin B$_1$, 2.5 μg/ml tryptophan and 100 μg/ml carbenecillin.

200 ml of medium was inoculated with 2–4 ml of an overnight culture of each clone (in the host E. coli HB101) grown in the above medium except for the presence of 42.5 μg/ml tryptophan, and grown at 37+ C. with vigorous aeration. At OD$_{600}$ of 0.5, indole acrylic acid, the inducer of the E. coli trp promoter and therefore also of IFN synthesis, was added to 20 μg/ml. At 4–5 hours after induction 3 ml of culture was withdrawn (OD$_{600}$=0.75–1.2 range) and split as follows: 1 ml was for estimation of total "solubilized" IFN antiviral or antiproliferative activity (the activity regained after a denaturation/renaturation cycle); and 1 ml was for display of the total accumulated E. coli proteins plus IFN in a polyacrylamide gel.

(a) Estimation of TOTAL "solubilized" IFN antiviral activity

For recovery of TOTAL "solubilized" IFN antiviral activity, the pellets were vortexed in 20 µl "lysis buffer" per 0.1 $OD_{600}$ per ml of culture. ("Lysis buffer" is 5M urea, 30 mM NaCl, 50 mM Tris-HCl pH7.5, 1% SDS, 1% 2-mercaptoethanol, 1% HSA). The mixture was heated for 2-3 minutes at 90° C., frozen at −70° C. for 15 minutes, thawed and centrifuged at 17K rpm for 20 minutes. The supernatant was diluted in 1 log steps to 1:10⁵, and appropriate dilutions immediately assayed for IFN antiviral activity by monitoring the protection conferred on Vero cells against the cytopathic effect (cpe) of EMC virus in an in vitro micro-plate assay system (e.g. see Dahl and Degre, Acta. Path. Microbiol. Scan., 1380, 863, 1972). The diluent was 50 mM Tris-HCl pH7.5, 30 mM NaCl, 1% human serum albumin (HSA).

(b) Polyacrylamide gel electrophoresis of total polypeptides

Cells from 1 ml of culture were mixed with 10 µl per 0.1 $OD_{600}$ per ml of final sample buffer: 5 M urea, 1% SDS, 1% 2-mercaptoethanol, 50 mM Tris-HCl pH7.5, 30 mM NaCl and 0.05% bromophenol blue. The mixture was heated at 90° C. for 5 minutes, centrifuged for 10 minutes and 5-7 µl loaded on a 15% acrylamide/0.4% bisacrylamide "Laemmli" gel. Electrophoresis was at 70 V for 18 hours. The gel was fixed and stained with Coomassie brilliant blue, then dried and photographed.

(c) Antiproliferative assays of modified, novel interferons

Antiproliferative activity was assessed by the ability of the IFN to inhibit the replication of Daudi lymphoblastoid cells (Horoszewicz et al, Science, 206, 1091, 1979). Daudi cells (in log phase) were cultured for 6 days in 96 well plates in the presence of various dilutions of interferon. The phenol red indicator in the medium changes from red to yellow (more acid) with progressive cell growth. Liquid paraffin was added to prevent pH change on exposure to the atmosphere and the pH change in the medium measured colorimetrically on a Dynatech plate reader. Interferon inhibition of cell growth is reflected by a corresponding reduction in the colour change.

Comparison of IFN protein expression, antiviral activity and antiproliferative activity in bacterial extracts Table 1 sets out the expression levels and antiproliferative and antiviral activities of the group III novel, modified IFNs in crude bacterial extracts. A range of activities may be given, reflecting natural variation in a biological system or assay. The activity quoted is that which is regained after SDS/urea/mercaptoethanol treatment, by diluting the extract in 1% human serum albumin, as above.

TABLE 1

| Novel modified IFN | IFNX No. | Expression (% of total cell protein) | EMC/Vero Antiviral activity IU/L/$OD_{600}$ | Daudi cell Antiproliferative activity Units/ml at $IC_{50}$* |
|---|---|---|---|---|
| $\beta$[82-105 → $\alpha_1$80-103] [Leu84→Pro] | 423 | >20 | 1.3-3.6 × 10⁷ | 1.3 × 10³ |
| $\beta$[82-105 → $\alpha_1$80-103] | 429 | >20 | 2 × 10⁸ | n.d. |
| IFN-$\beta$ control | — | 10 | 0.5-2 × 10⁸ | 3.4 × 10³ | n.d. = not done
*Units/ml at $IC_{50}$ = dilution of sample assayed for antiviral activity giving 50% inhibition of cell growth.

It may be seen in Table 1 that for the control, IFN-$\beta$, antiviral (AV) and antiproliferative (AP) activity vary over not more than a 4-fold range (>20 experiments). While the in vitro antiproliferative activity of IFNX423 is not significantly different from IFN-$\beta$, the antiviral activity is lower (∼3 to 30-fold). This may be due in part to the proline at amino acid residue 84, since IFNX429, which is identical to IFNX423 except for leucine at residue 84, displays similar antiviral activity to IFN-$\beta$. Therefore, shortening the predicted "C" $\alpha$-helix by the introduction of a proline may adversely affect in vitro antiviral activity. In conclusion, IFNX423 and IFNX429 are examples of novel, modified IFNs which have lost part of their antiviral activities.

Biological Properties of IFNX405

1. Methods

The expressed proteins were extracted from E. coli with the aid of sodium dodecyl sulphate (SDS) and purified by chromatography on AcA44. The IFNs had estimated purity of 70-90% based on polyacrylamide gel electrophoretic (PAGE) analysis.

The novel interferons were tested to determine their specific antiviral, antiproliferative and immunomodulatory activities. The following assay systems were employed:

(i) Antiviral assay
  (a) Cytopathic effect (CPE) assay with encephalomyocarditis (EMC) virus. This is a standard assay which measures the ability of interferon to protect cell monolayers against the cytopathic effect of EMC virus. The cell lines used were: Vero (African Green Monkey epithelial), WISH (amnion epithelial), MRC-5 (foetal lung fibroblast) and 17-1 (foetal lung fibroblast). Cell monolayers were established in 96 well flat-bottomed microtitre plates in DMEM medium containing 2% donor calf serum plus glutamine and antibiotics. Serial 1 in 2 dilutions of interferon were incubated with the cells at 37° for 18-24 hours, the supernatant discarded and an appropriate challenge dose of EMC virus in medium added. After incubation at 37° for a further 24 hours, the supernatants were discarded, the monolayers fixed with formol/saline and stained with crystal violet. The plates were read visually to establish the dilution of interferon giving 50% inhibition of the cytopathic effect.
  (b) Plaque reduction assay—using Herpes simplex type 2 (HSV-2) virus with Vero (monkey)

Chang (human) and MDBK (bovine cells). Confluent monolayers of cells were established in 96 well flat-bottomed microtitre plates. After incubation at 37° for 18 hours with dilutions of interferons, the cells were challenged with an appropriate number of plaque forming units of virus, overlaid with medium containing 0.5% carboxymethyl cellulose and incubated at 37° for 24 hours. After fixation and staining the plaques were counted microscopically and the counts expressed as a percentage of the mean maximum plaque counts in untreated control wells. Interferon titres are the reciprocal dilutions giving 50% reduction in plaque number/well.

(ii) Antiproliferative assay

Daudi cells in Dulbecco's Modified Eagles Medium (DMEM) were seeded at $2 \times 10^5$/ml (200 μl) in 96 well tissue culture plates. Interferons were added at the time of seeding and cells incubated at 37+ in a humidified 5% $CO_2$ atmosphere. After 22 hours, tritiated thymidine was added and the cells incubated for a further 2 hours after which they were harvested on a Flow cell harvester washed and treated with 5% trichloroacetic acid. Acid insoluble radioactivity was counted and inhibition of thymidine incorporation was taken as a measure of the antiproliferative activity of interferon.

(iii) Immunomodulatory assay (Natural Killer (NK) Cell Activity

Buffy coat cells separated from human peripheral blood by Ficoll/Hypaque sedimentation were suspended in supplemented RPMI 1640 medium and incubated overnight at 37° with interferon dilutions. After washing to remove interferon, these effect or cells were incubated at 37° for a further 4 hours with $^{51}Cr$-labelled K562 cells at effector to target cell ratios of 20:1 or 10:1. (K562 is a human tumour-derived cell line). After centrifugation an aliquot of the supernatant was removed for measurement of released radioactivity. Maximum $^{51}Cr$ release was obtained by repeated freeze-thawing of a target cell suspension and a background control obtained by measurement of $^{51}Cr$ release from target cells incubated without effector cells. Results were expressed as percentage specific $^{51}Cr$ release:

$$\frac{\text{Test sample} - \text{background}}{\text{Maximum release} - \text{background}} \times 100$$

2. Results (i) Antiviral activities (a) CPE assay—EMC virus

Table 2 lists the assay means for the hybrid IFNX405 and the recombinant-derived IFN-β measured against EMC virus in Vero and the four human cell lines. The activities are expressed in units/mg protein.

From the individual interferon means in different cell types contained in Table 2 and from the summary pooled data across all cell types it is seen that IFNX405 has activity very similar to that of IFN-β in the different cell lines.

TABLE 2

Antiviral activities of IFN-β and IFNX405 against encephalomyocarditis virus (IFN units/mg protein)

| PREPA-RATION | Mean activities in each cell line | | | | |
|---|---|---|---|---|---|
| | Vero | Chang | CELL LINE WISH | MRC-5 | 17-1 |
| IFN-β x | $1.5 \times 10^5$ | $5.2 \times 10^5$ | $8.4 \times 10^5$ | $1.5 \times 10^5$ | $7.1 \times 10^4$ |
| IFNX405 x | $1.4 \times 10^5$ | $2.6 \times 10^5$ | $1.0 \times 10^6$ | $1.5 \times 10^5$ | $5.5 \times 10^4$ |

| PREPARATION | POOLED MEAN | 95% CONFIDENCE LIMITS (u/mg) |
|---|---|---|
| IFN-β | $2.4 \times 10^5$ u/mg | $1.5-3.9 \times 10^5$ |
| IFNX405 | $1.4 \times 10^5$ u/mg | $0.8-2.3 \times 10^5$ |

($\bar{x}$ calculated based upon 3–5 assays)

For comparative purposes, the observed activities (in units/ml) of preparations of fibroblast IFN-β and leucocyte IFN-α are shown in Table 3. These natural interferons were not available in purified form and were used in the assays in dilute solutions containing large amounts of non-interferon protein. Thus, results with natural IFN-β and IFN-α cannot be quoted in units/mg and the results in Table 3 are not directly comparable with those of Table 2. Nevertheless, it can be seen that the activity of both natural interferons is sustained across the five cell lines within an interferon class with the exception that WISH cells appear slightly more sensitive to both IFN-β and IFN-α.

TABLE 3

Relative antiviral activities of natural interferon preparations against encephalomyocarditis virus in vero and human cell lines
Interferon units/ml

| PREPA-RATION | Vero | Chang | CELL LINE WISH | MRC-5 | 17-1 |
|---|---|---|---|---|---|
| Fibroblast-derived β x | $3.6 \times 10^4$ | $5.6 \times 10^4$ | $1.3 \times 10^5$ | $7.8 \times 10^4$ | $6.8 \times 10^4$ |
| Leucocyte-derived IFN-α x | $2.5 \times 10^2$ | $1.5 \times 10^2$ | $1.3 \times 10^3$ | 80 | 80 |

(b) Plaque reduction assays HSV-2

Similar estimates of antiviral activities obtained with HSV-2 by means of plaque reduction assays are given in Table 4. In this case the experiments were confined to the human Chang cells, primate Vero cells on bovine MDBK cells. IFNX405 has similar activity to IFN-β in Chang and Vero but reduced activity in MDBK.

The pattern of natural IFN-β and IFN-α against HSV-2 in these 3 cell lines is shown in Table 5, again expressed as units/ml rather than as specific activity as a result of impure IFNs. In contrast to some reported results from other laboratories, IFN-β reacts reasonably well with our MDBK cell line, producing antiviral activity at about the same dilution as Vero or Chang cells. On the other hand, the IFN-α standard reacted substantially better with MDBK cells than with either Vero or Chang cells.

TABLE 4

Antiviral activities of IFN-$\beta$ and IFNX405 against HSV-2 determined by plaque reduction assay
Interferon units/mg protein

| PREPARATION | CELL LINE | | |
|---|---|---|---|
| | Vero | Chang | MDBK |
| IFN-$\beta$ x | $1.2 \times 10^5$ | $4.7 \times 10^5$ | $2.5 \times 10^5$ |
| IFNX405 x | $5.4 \times 10^4$ | $2.0 \times 10^5$ | $1.8 \times 10^4$ |

TABLE 5

Relative antiviral activity of natural interferons against HSV-2 in monkey, human and bovine cells determined by plaque reduction assays
Interferon units/ml

| PREPARATION | CELL LINE | | |
|---|---|---|---|
| | Vero | Chang | MDBK |
| Fibroblast-derived IFN-$\beta$ x | $2.6 \times 10^4$ | $9.3 \times 10^4$ | $1.9 \times 10^4$ |
| Leucocyte-derived IFN-$\alpha$ x | 59 | 90 | $6.8 \times 10^3$ |

Summarizing the results of antiviral activity with RNA and DNA viruses in relevant cell types, Table 6 lists the activities of the recombinant and natural interferons against EMC and HSV-2 in Chang and Vero cells (data from Tables 2–5). There is no indication from these results of preferential activity of IFNX405 against one or other of the 2 virus types. The results from the 2 sets of assays are remarkably similar and are not significantly different. Thus the pooled mean antiviral activity against EMC virus shown in the analysis of variance to Table 2 is equally valid as an estimate of antiherpes activity and can be used as an overall indicator of specific antiviral activity of IFNX405.

TABLE 6

Relative antiviral activity against encephalomyocarditis virus and HSV-2 for IFN-$\beta$ and IFNX405 assayed in human and monkey cells
Interferons (unit/mg protein)

| IFN Preparation | Pooled mean activity EMC virus (from Table 1 analysis) | Pooled mean activity HSV-2 Vero and Chang cells |
|---|---|---|
| IFN-$\beta$ | $2.4 \times 10^5$ | $3.5 \times 10^5$ |
| IFNX405 | $1.4 \times 10^5$ | $1.3 \times 10^5$ |

(c) Comparative antiviral data with an atypical Chang cell line

One line of Chang conjunctival cells maintained in high passage (approx. X 160) has undergone a mutational change such that it is approximately 3 times more sensitive to IFN-$\beta$ than the normal low passage Chang cells which we have used in routine assays. At the same time, the atypical high passage Chang cells recognize and respond to IFN-$\alpha$ with a 100-fold increase in sensitivity compared to the parental low passage Chang cells. Comparative ratios of antiviral activity in high and low passage Chang cells can therefore be used to indicate a degree of $\alpha$-like property in a particular recombinant.

The results of profiling the recombinant IFNX405 in this way is shown in Table 7.

(ii) Antiproliferative activity

IFN-$\beta$ and IFNX405 were assayed for growth inhibitory activity against Daudi lymphoblastoid cells in at least 4 replicate assays. The mean results of these assays are given in Table 8, activities being expressed as the potein concentration required to prouce a 50% inhibition of maximum thymidine incorporation in untreated control cells (Inhibitory Dose$_{50}$). IFNX405 has lost activity, and although the loss is slight, it is significant as shown by analysis of variance.

TABLE 7

Antiviral activities of IFN-$\beta$ IFNX405 in a typical Chang cells compared with natural and interferons

| | Chang$^{-1}$ (High passage) | Chang (Routine low passage) | Ratio ChA/Ch |
|---|---|---|---|
| | Units/mg | | |
| IFN-$\beta$ | $1.6 \times 10^6$ | $5.2 \times 10^5$ | 3 |
| IFNX405 | $3.0 \times 10^5$ | $2.6 \times 10^5$ | 1 |
| | Units/ml | | |
| Fibroblast IFN-$\beta$ | $1.7 \times 10^5$ | $5.6 \times 10^4$ | 3 |
| Leucocyte IFN-$\alpha$ | $3.4 \times 10^4$ | $1.5 \times 10^2$ | 226 |

TABLE 8

Antiproliferative activity of IFN-$\beta$ and IFNX405 assayed in Daudi human lymphoblastoid cells
Inhibitory Dose$_{50}$ ($\mu$g/ml)

| PREPARATION | No. of replicate assays (n) | Corrected Mean ID$_{50}$ | 95% Confidence Limits |
|---|---|---|---|
| IFN-$\beta$ | 4 | 3.8 | 1.5–9.8 |
| IFNX405 | 6 | 7.1 | 3.2–15.5 |

(iii) Immunomodulatory activity-NK assay

IFN-$\beta$ and IFNX405 were also repeatedly assayed for ability to enhance natural killer (NK) cell activity, a total of 9–11 assays contributing to the results which are shown in Table 9. In a similar fashion to the antiproliferative activity, the specific NK stimulating activity is expressed as the protein dose concentration producing a 50% effect (Stimulating Dose $_{50}$).

IFNX405 has reduced NK stimulating activity being about 4-fold less active than IFN-$\beta$ parent. This difference is significant as shown in the analysis of variance.

TABLE 9

Immunostimulant activities of IFN-$\beta$ and IFNX405 assayed with human NK cells

| PREPARATION | No. of replicate assays (n) | Corrected Mean SD$_{50}$ | 95% Confidence Limits |
|---|---|---|---|
| IFN-$\beta$ | 11 | 3.4 | 2.1–5.4 |
| IFNX405 | 9 | 14.5 | 8.5–24.5 |

3. Conclusions

Mean specific activities for the antiviral, antiproliferative and immunomodulatory properties of each interferon are summarized in Table 10. (It should be noted that activity varies directly with the figures taken from antiviral assays but inversely with the figures quoted from ID$_{50}$ and SD$_{50}$ assays). For convenience these results have been indexed relative to the IFN-$\beta$ parent in the lower half of Table 10. From this analysis it may be seen that IFNX405 has identical antiviral activity to IFN-$\beta$ but has lost a small part of its antiproliferative and immunostimulating properties.

TABLE 10

Comparative summary of biological data for recombinant and natural interferons

| PREPA-RATION | Specific antiviral activity (u/mg) | Specific antiproliferative activity ($ID_{50}$ $\mu g/ml^{-1}$) | Specific immunostimulant activity ($SD_{50}$ $\mu g/ml^{-1}$) |
|---|---|---|---|
| IFN-$\beta$ | $2.4 \times 10^5$ | 3.8 | 3.4 |
| IFNX405 | $1.4 \times 10^5$ | 7.1 | 14.5 |
| | Indexed results (IFN-$\beta$ = 100) | | |
| IFN-$\beta$ | 100 | 100 | 100 |
| IFNX405 | 100 (58) | 54 | 23 |

Figures in brackets indicate actual calculated index where it is not significantly different from 100. In all other cases, differences from 100 are significant.

Pharmaceutical formulation and administration

The novel, modified interferons of the present invention can be formulated by methods well known for pharmaceutical compositions, wherein the active interferon is combined in admixture with a pharmaceutically acceptable carrier substance, the nature of which depends on the particular mode of administration being used. Remington's Pharmaceutical Sciences by E. W. Martin, hereby incorporated by reference, describes compositions and formulations suitable for delivery of the interferons of the present invention. For instance, parenteral formulations are usually injectable fluids that use physiologically acceptable fluids such as saline, balanced salt solutions, or the like as a vehicle. Oral formulations may be solid, e.g. tablet or capsule, or liquid solutions or suspensions.

The novel, modified interferons of the invention may be administered to humans or other animals on whose cells they are effective in various ways such as orally, intravenously, intramuscularly, intraperitoneally, intranasally, intradermally or subcutaneously. Administration of the interferon composition is indicated for patients with malignancies or neoplasms, whether or not immunosuppressed, or in patients requiring immunomodulation, or antiviral treatment. Dosage and dose rates may parallel those employed in conventional therapy with naturally occurring interferons—approximately $10^5$ to $10^8$ units daily. Dosages significantly above or below these levels may be indicated in long term administration or during acute short term treatment. A novel, modified interferon may be combined with other treatments or used in association with other chemotherapeutic or chemopreventive agents for providing therapy against the above mentioned diseases and conditions, or other conditions against which it is effective.

Modifications of the above described modes for carrying out the invention such as, without limitation, use of alternative vectors, alternative expression control systems, and alternative host micro-organisms and other therapeutic or related uses of the novel interferons, that are obvious to those of ordinary skill in the biotechnology, pharmaceutical, medical and/or related fields are intended to be within the scope of the following claims.

CHART 2a

Chemically synthesized sequence for IFNX423

NruI
CGA TCT TCC GTC AAGA CTC TTC CTC TAC TGG TTG GAA CGA AGA TCT GCC GGA TAAA TTCT
GCTAGAAGG CAG TTC TGA GAA GGA GA TGA CCAA CCT TGC TTC TAGA CGG CCTA TTT AAGA

GCA CCGAA CTG TA CCAG CAA CTGAA CGA CCT GGAAG CA TG TGT TA TGC AGG AAC TGG AAA
CG TGG CTT GAC A TGG TCG TTG AC TTG CTG GAC CTT CG TA CAC AA TA CG TCC TTG ACC TTT

AAGAAGA CTT CA CCC GC
TTCTTCTGAAGTGGG
        SacII

CHART 2b

Chemically synthesized sequence for IFNX423

NruI
CGA TCT TCC GTC AAGA CTC TTC CTC TAC TGG TTG GAA CGA AGA TCT GCT GGA TAAA TTCT
GCTAGAAGG CAG TTC TGA GAA GGA GA TGA CCAA CCT TGC TTC TAGA CGA CCTA TTT AAGA

GCA CCGAA CTG TA CCAG CAA CTGAA CGA CCT GGAAG CA TG TGT TA TGC AGG AAC TGG AAA
CG TGG CTT GAC A TGG TCG TTG AC TTG CTG GAC CTT CG TA CAC AA TA CG TCC TTG ACC TTT

AAGAAGA CTT CA CCC GC
TTCTTCTGAAGTGGG
        SacII

Chart 2c

Chemically synthesized sequence for IFNX405

| MboII | | MboII |
|---|---|---|
| ATG CAAGAAGAA CGGG TTGG TGAAA CCC CGA | | |
| CTA CGT TCT TCT TGC CCA ACC A CTT TGGG GC | | |

CHART 3a

IFNX423

IFN-$\beta$[IFN-$\beta^{82-105}$⟶IFN-$\alpha^{80-103}$][Leu$^{84}$⟶Pro]

| | | | | 5 | | | | | 10 | | | | | 15 |
|---|---|---|---|---|---|---|---|---|---|---|---|---|---|---|
| MET | SER | TYR | ASN | LEU | LEU | GLY | PHE | LEU | GLN | ARG | SER | SER | ASN | PHE |
| ATG | AGC | TAC | AAC | TTG | CTT | GGA | TTC | CTA | CAA | AGA | AGC | AGC | AAT | TTT |

CHART 3a-continued

IFNX423

IFN-β[IFN-β$^{82-105}$ ⟶ IFN-α$^{80-103}$][Leu$^{84}$ ⟶ Pro]

```
                    20                              25                          30
GLN CYS GLN LYS LEU LEU TRP GLN LEU ASN GLY ARG LEU GLU TYR
CAG TGT CAG AAG CTC CTG TGG CAA TTG AAT GGG AGG CTT GAA TAC 35                          40                          45
CYS LEU LYS ASP ARG MET ASN PHE ASP ILE PRO GLU GLU ILE LYS
TGC CTC AAG GAC AGG ATG AAC TTT GAC ATC CCT GAG GAG ATT AAG 50                          55                              60
GLN LEU GLN GLN PHE GLN LYS GLU ASP ALA ALA LEU THR ILE TYR
CAG CTG CAA CAG TTC CAA AAA GAA GAT GCA GCG CTG ACT ATC TAC

NruI
                             ↓
                65                  70                          75
GLU MET LEU GLN ASN ILE PHE ALA ILE PHE ARG GLN ASP SER SER
GAA ATG CTG CAA AAC ATC TTC GCG ATC TTC CGT CAA GAC TCT TCC 80                          85                          90
SER THR GLY TRP ASN GLU ASP LEU PRO ASP LYS PHE CYS THR GLU
TCT ACT GGT TGG AAC GAA GAT CTG CCG GAT AAA TTC TGC ACC GAA 95                          100                         105
LEU TYR GLN GLN LEU ASN ASP LEU GLU ALA CYS VAL MET GLN GLU
CTG TAC CAG CAA CTG AAC GAC CTG GAA GCA TGT GTT ATG CAG GAA

SacII
                                         ↓
                110                         115                         120
LEU GLU LYS GLU ASP PHE THR ARG GLY LYS LEU MET SER SER LEU
CTG GAA AAA GAA GAC TTC ACC CGC GGT AAA CTG ATG AGC TCC CTG 125                         130                         135
HIS LEU LYS ARG TYR TYR GLY ARG ILE LEU HIS TYR LEU LYS ALA
CAT CTG AAA CGC TAC TAT GGT CGT ATC CTG CAT TAC CTG AAA GCT 140                         145                         150
LYS GLU TYR SER HIS CYS ALA TRP THR ILE VAL ARG VAL GLU ILE
AAA GAA TAC TCT CAC TGC GCA TGG ACT ATT GTA CGC GTT GAA ATC 155                         160                         165
LEU ARG ASN PHE TYR PHE ILE ASN ARG LEU THR GLY TYR LEU ARG
CTG CGT AAC TTC TAC TTC ATC AAC CGC CTG ACT GGT TAC CTG CGT

ASN ***
AAC TAA
```

```
            10              20              30              40              50
MSYNLLGFLQ—RSSNFQCQKL—LWQLNGRLEY—CLKDRMNFDI—PEEIKQLQQF—

60              70              80              90              100
QKEDAALTIY—EMLQNIFAIF—RQDSSSTGWN—EDLPDKFCTE—LYQQLNDLEA—

110             120             130             140             150
CVMQELEKED—FTRGKLMSSL—HLKRYYGRIL—HYLKAKEYSH—CAWTIVRVEI—

160       /
LRNFYFINRL—TGYLRN
                  \
```

CHART 3b

IFNX429

IFN-β[IFN-β$^{82-105}$ ⟶ IFN-α$^{80-103}$]

```
        1   2   3   4   5   6   7   8   9   10  11  12  13  14  15
       MET SER TYR ASN LEU LEU GLY PHE LEU GLN ARG SER SER ASN PHE
       ATG AGC TAC AAC TTG CTT GGA TTC CTA CAA AGA AGC AGC AAT TTT 16  17  18  19  20  21  22  23  24  25  26  27  28  29  30
       GLN CYS GLN LYS LEU LEU TRP GLN LEU ASN GLY ARG LEU GLU TYR
       CAG TGT CAG AAG CTC CTG TGG CAA TTG AAT GGG AGG CTT GAA TAC 31  32  33  34  35  36  37  38  39  40  41  42  43  44  45
       CYS LEU LYS ASP ARG MET ASN PHE ASP ILE PRO GLU GLU ILE LYS
       TGC CTC AAG GAC AGG ATG AAC TTT GAC ATC CCT GAG GAG ATT AAG 46  47  48  49  50  51  52  53  54  55  56  57  58  59  60
       GLN LEU GLN GLN PHE GLN LYS GLU ASP ALA ALA LEU THR ILE TYR
       CAG CTG CAA CAG TTC CAA AAA GAA GAT GCA GCG CTG ACT ATC TAC
```

NruI ↓

```
       61  62  63  64  65  66  67  68  69  70  71  72  73  74  75
       GLU MET LEU GLN ASN ILE PHE ALA ILE PHE ARG GLN ASP SER SER
       GAA ATG CTG CAA AAC ATC TTC GCG ATC TTC CGT CAA GAC TCT TCC 76  77  78  79  80  81  82  83  84  85  86  87  88  89  90
       SER THR GLY TRP ASN GLU ASP LEU LEU ASP LYS PHE CYS THR GLU
       TCT ACT GGT TGG AAC GAA GAT CTG CTG GAT AAA TTC TGC ACC GAA 91  92  93  94  95  96  97  98  99  100 101 102 103 104 105
       LEU TYR GLN GLN LEU ASN ASP LEU GLU ALA CYS VAL MET GLN GLU
       CTG TAC CAG CAA CTG AAC GAC CTG GAA GCA TGT GTT ATG CAG GAA
```

SacII ↓

```
       106 107 108 109 110 111 112 113 114 115 116 117 118 119 120
       LEU GLU LYS GLU ASP PHE THR ARG GLY LYS LEU MET SER SER LEU
       CTG GAA AAA GAA GAC TTC ACC CGC GGT AAA CTG ATG AGC TCC CTG 121 122 123 124 125 126 127 128 129 130 131 132 133 134 135
       HIS LEU LYS ARG TYR TYR GLY ARG ILE LEU HIS TYR LEU LYS ALA
       CAT CTG AAA CGC TAC TAT GGT CGT ATC CTG CAT TAC CTG AAA GCT 136 137 138 139 140 141 142 143 144 145 146 147 148 149 150
       LYS GLU TYR SER HIS CYS ALA TRP THR ILE VAL ARG VAL GLU ILE
       AAA GAA TAC TCT CAC TGC GCA TGG ACT ATT GTA CGC GTT GAA ATC 151 152 153 154 155 156 157 158 159 160 161 162 163 164 165
       LEU ARG ASN PHE TYR PHE ILE ASN ARG LEU THR GLY TYR LEU ARG
       CTG CGT AAC TTC TAC TTC ATC AAC CGC CTG ACT GGT TAC CTG CGT

ASN ***
       AAC TAA
```

```
              10          20          30          40          50
       MSYNLLGFLQ—RSSNFQCQKL—LWQLNGRLEY—CLKDRMNFDI—PEEIKQLQQF—

60          70          80          90         100
       QKEDAALTIY—EMLQNIFAIF—RQDSSSTGWN—EDLLDKFCTE—LYQQLNDLEA—

110         120         130         140         150
       CVMQELEKED—FTRGKLMSSL—HLKRYYGRIL—HYLKAKEYSH—CAWTIVRVEI—
```

CHART 3b-continued

IFNX429

IFN-β[IFN-β$^{82-105}$ ⟶ IFN-α$^{80-103}$]

```
         160        /
LRNFYFINRL—TGYLRN
                    \
```

CHART 3c

Synthetic IFN-β gene

<u>ClaI</u>                                                                                    <u>PstI</u>
                                                                                5          10
                    MET SER TYR ASN LEU LEU GLY PHE LEU GLN
        CGA TAA GCT ATG TCT TAC AAC CRG CRG GGC TTC CTG CAG 15                      20
        ARG SER SER ASN PHE GLN CYS GLN LYS LEU LEU TRP GLN
        CGT TCT TCT AAC TTC CAA TGC CAG AAA CRG CRG RGG CAA

<u>XmaIII</u>
            25                    30                    35
        LEU ASN GLY ARG LEU GLU TYR CYS LEU LYS ASP ARG MET
        CTG AAC GGC CGC CTG GAA TAC TGC CTG AAA GAC CGC ATG

<u>PvuII</u>
                        41              45
        ASN PHE ASP ILE PRO GLU GLU ILE LYS GLN LEU GLN GLN
        AAC TTT GAT ATC CCA GAA GAA ATC AAA CAG CTG CAA CAG 50                      55                      60
        PHE GLN LYS GLU ASP ALA ALA LEU THR ILE TYR GLU MET
        TTC CAA AAA GAA GAT GCA GCG CTG ACT ATC TAC GAA ATG

<u>NruI</u>              <u>HinfI</u>
                65                      71              75
        LEU GLU ASN ILE PHE ALA ILE PHE ARG GLN ASP SER SER
        CTG CAA AAC ATC TTC GCG ATC TTC CGT CAA GAC TCT TCC 80                  85
        SER THR GLY TRP ASN GLU THR ILE VAL GLU ASN LEU LEU
        TCT ACT GGT TGG AAC GAA ACT ATC GTA GAA AAC CTG CTG <u>AccI</u>
            90                  95                  100
        ALA ASN VAL TYR HIS GLN ILE ASN HIS LEU LYS THR VAL
        GCA AAC GTA TAC CAT CAG ATC AAC CAT CTG AAA ACC GTG <u>SacII</u>
                        105                 110
        LEU GLU GLU LYS LEU GLU LYS GLU ASP PHE THR ARG GLY
        CTG GAA GAG AAA CTG GAA AAA GAA GAC TTC ACC CGC GGT <u>SacI</u>
        115                         122             125
        LYS LEU MET SER SER LEU HIS LEU LYS ARG TYR TYR GLY
        AAA CTG ARG AGC TCC CTG CAT CTG AAA CGC TAC TAT GGT 130                 135                 140
        ARG ILE LEU HIS TYR LEU LYS ALA LYS GLU TYR SER HIS
        CGT ATC CTG CAT TAC CTG AAA GCT AAA GAA TAC TCT CAC <u>MstI</u>
                            145                 150
        CYS ALA TRP THR ILE VAL ARG VAL GLU ILE LEU ARG ASN
        TGC GCA TGG ACT ATT GTA CGC GTT GAA ATC CTG CGT AAC

CHART 3c-continued

Synthetic IFN-β gene

```
                                   BstEII
       155                    160                       166
   PHE TYR PHE ILE ASN ARG LEU THR GLY TYR LEU ARG ASN
   TTC TAC TTC ATC AAC CGC CTG ACT GGT TAC CTG CGT AAC

BamHI
   TER
   TAA GAA TCC
```

R⟨ AMSYNLLGFLQRSSNFQCQKLLWQLNGRLEYCLKDRMNFDIPEEIKQLQQF

QKEDAALTIYEMLQNIFAIFRQDSSSTGWNETIVENLLANVYHQINHLKTVLE

EKLEKEDFTRGKLMSSLHLKRYYGRILHYLKAKEYSHCAWTIVRVEILRNFYF

INRLTGYLRN⟨ GS

CHART 3d

IFNX405

$$\text{IFN-}\beta[\text{IFN-}\beta(\beta^{103\text{-}112} \longrightarrow \alpha_1^{101\text{-}110})]$$

```
                         5                        10                         15
  MET SER TYR ASN LEU LEU GLY PHE LEU GLN ARG SER SER ASN PHE
  ATG AGC TAC AAC TTG CTT GGA TTC CTA CAA AGA AGC AGC AAT TTT 20                       25                         30
  GLN CYS GLN LYS LEU LEU TRP GLN LEU ASN GLY ARG LEU GLU TYR
  CAG TGT CAG AAG CTC CTG TGG CAA TTG AAT GGG AGG CTT GAA TAC 35                       40                         45
  CYS LEU LYS ASP ARG MET ASN PHE ASP ILE PRO GLU GLU ILE LYS
  TGC CTC AAG GAC AGG ATG AAC TTT GAC ATC CCT GAG GAG ATT AAG 50                       55                         60
  GLN LEU GLN GLN PHE GLN LYS GLU ASP ALA ALA LEU THR ILE TYR
  CAG CTG CAA CAG TTC CAA AAA GAA GAT GCA GCG CTG ACT ATC TAC 65                       70                         75
  GLU MET LEU GLN ASN ILE PHE ALA ILE PHE ARG GLN ASP SER SER
  GAA ATG CTG CAA AAC ATC TTC GCG ATC TTC CGT CAA GAC TCT TCC 80                       85                         90
  SER THR GLY TRP ASN GLU THR ILE VAL GLU ASN LEU LEU ALA ASN
  AGC ACT GGC TGG AAT GAG ACT ATT GTT GAG AAC CTC CTG GCT AAT

MboII
                                                     ↓
                         95                      100                        105
  VAL TYR HIS GLN ILE ASN HIS LEU LYS THR VAL LEU MET GLN GLU
  GTC TAT CAT CAG ATA AAC CAT CTG AAG ACA GTC CTG ATG CAA GAA (MboII)
                        110                       115                        120
  GLU ARG VAL GLY GLU THR PRO ARG GLY LYS LEU MET SER SER LEU
  GAA CGG GTT GGT GAA ACC CCG AGG GGA AAA CTC ATG AGC AGT CTG 125                       130                        135
  HIS LEU LYS ARG TYR TYR GLY ARG ILE LEU HIS TYR LEU LYS ALA
  CAC CTG AAA AGA TAT TAT GGG AGG ATT CTG CAT TAC CTG AAG GCC
```

CHART 3d-continued

IFNX405

IFN-β[IFN-β(β$^{103-112}$ ⟶ α$_1$$^{101-110}$)]

```
              140                   145                         150
LYS GLU TYR SER HIS CYS ALA TRP THR ILE VAL ARG VAL GLU ILE
AAR GAG TAC AGT CAC TGT GCC TGG ACC ATA GRC AGA GTG GAA ATC 155                   160                         165
LEU ARG ASN PHE TYR PHE ILE ASN ARG LEU THR GLY TYR LEU ARG
CTA AGG AAC TTT TAC TTC ATT AAC AGA CTT ACA GGT TAC CTC CGA

ASN ***
AAC TGA
```

```
         10           20           30           40           50
MSYNLLGFLQ—RSSNFQCQKL—LWQLNGRLEY—CLKDRMNFDI—PEEIKQLQQF—

60           70           80           90          100
QKEDAALTIY—EMLQNIFAIF—RQDSSSTGWN—ETIVENLLAN—VYHQINHLKT—

110          120          130          140          150
VLMQEERVGE—TPRGKLMSSL—HLKRYYGRIL—HYLKAKEYSH—CAWTIVRVEI—

160
LRNFYFINRL—TGYLRN
```

CHART 4

Nucleotide sequence of trp promoter region of IFN-β expression plasmid pl-24/C

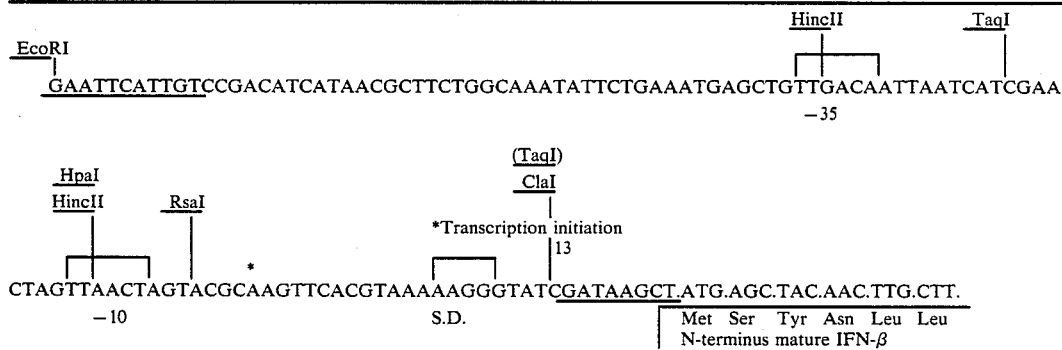

We claim:

1. A modified beta interferon comprising a beta interferon wherein amino acids 82 to 105 of said beta interferon are replaced by amino acids 80 to 103 of alpha 1 interferon.

2. A modified beta interferon comprising a beta interferon wherein amino acids 82 to 105 of said beta interferon are replaced by amino acids 80 to 103 of alpha 1 interferon with the exception that the leucine which is located at position 84 of natural beta interferon is replaced by proline.

3. A modified beta interferon comprising a beta interferon wherein amino acids 103 to 112 of said beta interferon are replaced by amino acids 101 to 110 of alpha 1 interferon.

4. A pharmaceutical composition for use in the treatment of viral infections in an animal comprising an effective therapeutic amount of the modified beta interferon of claim 1 admixed with a pharmaceutically acceptable carrier.

5. A pharmaceutical composition for use in the treatment of viral infections in an animal comprising an effective therapeutic amount of the modified beta interferon of claim 2 admixed with a pharmaceutically acceptable carrier.

6. A pharmaceutical composition for use in the treatment of viral infections, or neoplastic disease or for stimulating the immune system in an animal comprising an effective therapeutic amount of the modified beta interferon of claim 3 admixed with a pharmaceutically acceptable carrier.

7. A method of treating viral infections in an animal in need of such treatment comprising the administration of an effective amount of the modified beta interferon of claim 3.

8. A method of regulating cell growth in an animal in need of such treatment comprising the administration of an effective amount of the modified beta interferon of claim 3.

9. A method of regulating the immune system in an animal in need of such treatment comprising the administration of an effective amount of the modified beta interferon of claim 3.

* * * * *

UNITED STATES PATENT AND TRADEMARK OFFICE
CERTIFICATE OF CORRECTION

PATENT NO. : 4,753,795

DATED : June 28, 1988

INVENTOR(S) : Bell, et al.

It is certified that error appears in the above-identified patent and that said Letters Patent is hereby corrected as shown below:

Column 4, line 34, reading "residues 85-115" should read -- residues 82-115 --.

Column 7, line 42, reading "$\beta$-helix" should read --$\alpha$-helix --.

Column 8, that portion of the vector reading

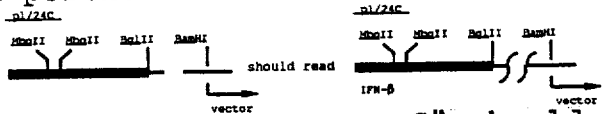

Column 8, lines 58-59, reading "37+C" should read -- $37^a$C --.

Column 11, line 21, reading "37+" should read -- $37^a$ --.

Column 14, lines 2-3, reading "potein concentration required to prouce" should read -- protein concentration required to produce --.

Columns 15-16, the heading of Chart 2b, reading "IFNX423" should read -- IFNX429 --.

Columns 19-20 and Columns 21-22, the heading of Chart 3b, reading "IFN-$\alpha^{80-103}$]" should read -- IFN-$\alpha_1^{80-103}$] --.

Columns 21-22, Chart 3C, the nucleotide sequence of the codon coding for amino acid LEU at position 5, reading "CRG" should read -- CTG --.

In addition to above correction, Columns 21-22, Chart 3c, the position of the number "5" labeling the 5th position should be moved over to the left 3 positions so that $_5$LEU reads LEU CRG  $_5$CTG Columns 21-22, Chart 3c, the nucleotide sequence of the codon coding for amino acid LEU at position 6, reading "CRG" should read -- CTG --.

Columns 21-22, Chart 3c, the nucleotide sequence of the codon coding for amino acid LEU at position 20, reading "CRG" should read -- CTG --.

UNITED STATES PATENT AND TRADEMARK OFFICE
CERTIFICATE OF CORRECTION

PATENT NO. : 4,753,795

DATED : June 28, 1988

INVENTOR(S) : Bell, et al.

It is certified that error appears in the above-identified patent and that said Letters Patent is hereby corrected as shown below:

Columns 21-22, Chart 3c, the nucleotide sequence of the codon coding for amino acid LEU at position 21, reading "CRG" should read -- CTG --.

Columns 21-22, Chart 3c, the nucleotide sequence of the codon coding for amino acid TRP at position 22, reading "RGG" should read -- TGG --.

Columns 21-22, Chart 3c, the amino acid of the nucleotide sequence at position 64, reading "GLU" should read -- GLN --.

Columns 23-24, Chart 3d, the nucleotide sequence of the codons coding for amino acids at positions 51-58, reading

```
                    55
GLN LYS GLU ASP ALA ALA LEU THR
CAA AAA GAA GAT GCA GCG CTG ACT      should read

55
GLN LYS GLU ASP ALA ALA LEU THR
CAG AAG GAG GAC GCC GCA TTG ACC
```

Columns 23-24, Chart 3d, the nucleotide sequence of the codons coding for amino acids TYR and GLU at positions 60 and 61, reading "TAC GAA" should read -- TAT GAG --.

Columns 23-24, Chart 3d, the nucleotide sequence of the codons coding for amino acids LEU and GLN at positions 63 and 64, reading "CTG CAA" should read -- CTC CAG --.

Columns 23-24, Chart 3d, the nucleotide sequence of the codons coding for amino acids PHE, ALA and ILE at positions 67-69, reading "TTC GCG ATC" should read -- TTT GCT ATT --.

Columns 23-24, Chart 3d, the nucleotide sequence of the codons coding for amino acid ARG at positon 71, reading "CGT" should read -- AGA --.

UNITED STATES PATENT AND TRADEMARK OFFICE
CERTIFICATE OF CORRECTION

PATENT NO. : 4,753,795

DATED : June 28, 1988

INVENTOR(S) : Bell, et al.

Page 3 of 3

It is certified that error appears in the above-identified patent and that said Letters Patent is hereby corrected as shown below:

Columns 23-24, Chart 3d the nucleotide sequence of the codons coding for amino acids ASP, SER and SER at positions 73-75, reading "GAC TCT TCC" should read -- GAT TCA TCT --.
Columns 25-26, Chart 3d, the nucleotide sequence of the codon coding for amino acid LYS at position 136, reading "AAR" should read -- AAG --.
Columns 25-26, Chart 3d, the nucleotide sequence of the codon coding for amino acid VAL at position 146, reading "GRC" should read -- GTC --.
Columns 25-26, Chart 4, reading EcoRI
|
GAATTCATTGTCCGACATCATAACGC          should read EcoRI
|
GAATTCATTGTCCGACATCATAACGG (i.e., the last letter of the sequence should be "G" instead of "C").

Signed and Sealed this

Third Day of April, 1990

Attest:

HARRY F. MANBECK, JR.

Attesting Officer

Commissioner of Patents and Trademarks